United States Patent
McCollough et al.

(10) Patent No.: US 9,869,641 B2
(45) Date of Patent: Jan. 16, 2018

(54) MICROWAVE IMAGING DEVICE

(71) Applicant: ELLUMEN, INC., Arlington, VA (US)

(72) Inventors: William J. McCollough, Earlysville, VA (US); Todd R. McCollough, Barrington, IL (US); Wenyi Shao, Laurel, MD (US); Arezou Edalati, Arlington, VA (US); John Ryan Leslie, Arlington, VA (US)

(73) Assignee: ELLUMEN, INC., Arlington, VA (US)

( * ) Notice: Subject to any disclaimer, the term of this patent is extended or adjusted under 35 U.S.C. 154(b) by 71 days.

(21) Appl. No.: 15/094,368

(22) Filed: Apr. 8, 2016

(65) Prior Publication Data

US 2017/0292919 A1   Oct. 12, 2017

(51) Int. Cl.
*G01R 27/04* (2006.01)
*G01R 27/32* (2006.01)
(Continued)

(52) U.S. Cl.
CPC ........... *G01N 22/00* (2013.01); *G01R 27/00* (2013.01); *G01R 27/06* (2013.01); *G01R 27/28* (2013.01); *G01R 31/11* (2013.01); *G01R 27/04* (2013.01)

(58) Field of Classification Search
CPC ........ G01N 22/00; G01R 27/06; G01R 27/28; G01R 31/11; G01R 27/00; G01R 27/04; G01R 27/32
(Continued)

(56) References Cited

U.S. PATENT DOCUMENTS

| 5,103,181 A | 4/1992 | Gaisford et al. |
| 5,841,288 A | 11/1998 | Meaney et al. |

(Continued)

FOREIGN PATENT DOCUMENTS

| KR | 10201140520 A | 4/2011 |
| WO | WO-2011/163359 A2 | 12/2011 |
| WO | WO-2014/126540 A1 | 8/2014 |

OTHER PUBLICATIONS

Andrea Salvade et al, A New Microwave Axial Tomograph for the Inspection of Dielectric Materials, IEEE Transactions on Instrumentation and Measurement, vol. 58, No, 7, Jul. 2009, pp. 2072-2079.

(Continued)

*Primary Examiner* — Jermele M Hollington
*Assistant Examiner* — Raul Rios Russo
(74) *Attorney, Agent, or Firm* — Foley & Lardner LLP

(57) ABSTRACT

A microwave (MW) system includes an object support adapted to support an object, a MW transmitter, a MW receiver, an outer rotation unit, an inner rotation unit, a controller and a computation processor. The outer rotation unit includes an outer ring, having a ring shape, with an outer ring mount, upon which one of either an antenna of the MW transmitter or an antenna of the MW receiver is mounted. The inner rotation unit comprises an inner ring, having a ring shape, with an inner ring mount, upon which the other of an antenna of the MW transmitter or an antenna of the MW receiver is mounted. The controller is configured to independently control both the rotation of the inner ring and the outer ring. The computation processor is configured to receive data including MW data representative of MW scattered field detected by the MW receiver.

27 Claims, 7 Drawing Sheets

(51) Int. Cl.
  *G01N 22/00* (2006.01)
  *G01R 27/28* (2006.01)
  *G01R 27/06* (2006.01)
  *G01R 31/11* (2006.01)
  *G01R 27/00* (2006.01)

(58) Field of Classification Search
  USPC .......... 324/76.11–76.83, 459, 600, 629, 637
  See application file for complete search history.

(56) References Cited

U.S. PATENT DOCUMENTS

| | | | |
|---|---|---|---|
| 5,995,863 | A | 11/1999 | Farace et al. |
| 6,175,768 | B1 | 1/2001 | Arndt et al. |
| 6,433,720 | B1 | 8/2002 | Libove et al. |
| 6,448,788 | B1 | 9/2002 | Meaney et al. |
| 6,972,714 | B1 | 12/2005 | Baharav et al. |
| 7,040,168 | B1 | 5/2006 | Merkel |
| 7,132,836 | B2 | 11/2006 | Peters et al. |
| 7,280,227 | B2 | 10/2007 | Merkel et al. |
| 7,378,855 | B2 | 5/2008 | Moshe |
| 7,550,969 | B2 | 6/2009 | Zhdanov |
| 7,746,266 | B2 | 6/2010 | Zoughi et al. |
| 7,804,309 | B2 | 9/2010 | Cummins |
| 7,809,427 | B2 | 10/2010 | Winters et al. |
| 7,825,667 | B2 | 11/2010 | Fang et al. |
| 7,933,786 | B2 | 4/2011 | Wargin et al. |
| 8,089,417 | B2 | 1/2012 | Popovic et al. |
| 8,095,204 | B2 | 1/2012 | Smith et al. |
| 8,207,733 | B2 | 6/2012 | Meaney et al. |
| 8,400,168 | B2 | 3/2013 | Troxler et al. |
| 9,111,334 | B2 | 8/2015 | McCollough et al. |
| 2004/0077943 | A1 | 4/2004 | Meaney et al. |
| 2005/0203387 | A1 | 9/2005 | Godshalk et al. |
| 2008/0211726 | A1 | 9/2008 | Elsallal et al. |
| 2008/0319285 | A1 | 12/2008 | Hancock |
| 2009/0015832 | A1 | 1/2009 | Popovic et al. |
| 2009/0027288 | A1 | 1/2009 | Lee et al. |
| 2009/0273509 | A1 | 11/2009 | Fullerton |
| 2010/0113921 | A1 | 5/2010 | Fear et al. |
| 2010/0145190 | A1 | 6/2010 | Bourqui et al. |
| 2011/0006785 | A1 | 1/2011 | Gradinarsky |
| 2011/0028825 | A1 | 2/2011 | Douglas et al. |
| 2011/0119212 | A1 | 5/2011 | De Bruin et al. |
| 2011/0130656 | A1 | 6/2011 | Son et al. |
| 2011/0169933 | A1 | 7/2011 | Touboul |
| 2012/0019406 | A1 | 1/2012 | Sarkis |
| 2012/0128265 | A1 | 5/2012 | Silver et al. |
| 2012/0158739 | A1 | 6/2012 | Ah-Pine et al. |
| 2012/0177267 | A1 | 7/2012 | Chen et al. |
| 2012/0328076 | A1 | 12/2012 | Ikhlef |
| 2012/0330151 | A1 | 12/2012 | Weinstein et al. |
| 2013/0018591 | A1 | 1/2013 | Grzegorczyk |
| 2014/0003699 | A1 | 1/2014 | Moulik |
| 2014/0218230 | A1* | 8/2014 | Ostadrahimi .......... G01N 22/00 342/179 |
| 2015/0208945 | A1* | 7/2015 | Lux ...................... A61B 5/0507 600/430 |
| 2016/0198975 | A1* | 7/2016 | Gibbins ................. G01N 22/00 600/430 |

OTHER PUBLICATIONS

Elise C. Fear et al., Enhancing Breat Tumor Detection with Near-Field Imaging, IEEE Microwave Magazine, Mar. 2002, pp. 49-56.
Mariya Lazebnik et al., Highly Accurate Debye Models for Normal and Malignant Breast Tissue Dielectric Properties at Microwave Frequencies, IEEE Microwave and Wireless Components Letters, vol. 17, No. 12, Dec. 2007, pp. 822-824.
USPTO Notice of Allowance, U.S. App. No. 14/069,661, dated Apr. 14, 2015, 10 pages.
Jeremie Bourqui et al., Measurement and Analysis of Microwave Frequency Signals Transmitted Through the Breast, Research Article, International Journal of Biomedical Imaging, 2012, 11 pages.
N. A. Simonov et al., 3D Microwave Breast Imaging Based on Multistatic Radar Concept System, Electronics and Telecommunications Research Institute, Sep. 2011, 4 pages.
U.S. Appl. No. 14/054,105, filed Oct. 15, 2013, The University of North Carolina at Charlotte.
U.S. Appl. No. 15/177,511, filed Jun. 9, 2016, Ellumen, Inc.
A. Randazzo Targets, et al., A Multistatic Tomographic Approach to Microwave Imaging of Dielectric Targets, EuCAP, 2011, pp. 2790-2794.
Aaron Zachary Hood et al., A Small Antipodal Vivaldi Antenna for Ultrawide-Band Applications, IEEE Antennas and Wireless Propagation Letters, vol. 7, 2008, pp. 656-660.
Andrea Salvade et al, A New Microwave Axial Tomograph for the Inspection of Dielectric Materials, IEEE Transactions on Instrumentation and Measurement, vol. 58, No. 7, Jul. 2009, pp. 2072-2079.
Andreas Christ et al., The Virtual Family—Development of Surface-Based Anatomical Models of Two Adults and Two Children for Dosimetric Simulations, Physics in Medicine and Biology 55, 2010, pp. N23-N38.
Ann Franchois et al., Microwave Imaging-Complex Permittivity Reconstruction with a Levenberg-Marquardt Method, IEEE Transactions on Antennas and Propagation, Feb. 1997, pp. 203-215, vol. 45, No. 2.
Beibei Zhou et al., UWB Microwave Imaging for Early Breast Cancer Detection: Effect of the Coupling Medium on Resolution, IEEE, 2004, pp. 431-434.
C. Gabriel et al., The Dielectric Properties of Biological Tissues: I. Literature Survey, Phys. Med. Biol. 41, 1996, pp. 2231-2249.
Chou et al., Development of a Rat Head Exposure System for Simulating Human Exposure to RF Fields from Handheld Wireless Telephones, Bioelectromagnetics, Suppl. Issue, n4, 1999, pp. 75-92.
Christian Weber, Development of Patient-Specific Electromagnetic Model (PSEM) Based on MR Breast Images, Sep. 27, 2010, pp. 1-36.
D.C. Zhu et al., Brain Water Content Measurement and Visualization With Applications to Hydrocephalus, Proc. Intl. Soc. Mag. Reson. Med. 13, 2005, pp. 1099.
Daniel R. Messroghli et al., An Open-Source Software Tool for the Generation of Relaxation Time Maps in Magnetic Resonance Imaging, BMC Medical Imaging, 2010, 10:16, pp. 1-8.
David C. Zhu et al., Full-Brain T1 Mapping Through Inversion Recovery Fast Spin Echo Imaging With Time-Efficient Slice Ordering, Magnetic Resonance in Medicine, 54, 2005, pp. 725-731.
Elise C. Fear et al., Confocal Imaging for Breast Cancer Detection: Localization of Tumors in Three Dimensions, IEEE Transactions on Biomedical Engineering, Aug. 2002, pp. 812-822, vol. 49, No. 8.
Elise C. Fear et al., Enhancing Breast Tumor Detection with Near-Field Imaging, IEEE Microwave Magazine, Mar. 2002, pp. 49-56.
Elise Fear et al., Microwaves for Breast Cancer Detection?, IEEE Potentials, 2003, pp. 12-18.
Gary A. Ybarra et al., Microwave Breast Imaging, Emerging Technology in Breast Imaging and Mammography, 2007, Chapter 16, pp. 1-12.
H. Neeb et al., A New Method for Fast Quantitative Mapping of Absolute Water Content in VIVO, NeuroImage 31, 2006, pp. 1156-1168.
Hoi-Shun Lui et al., Development of Patient-Specific Breast Electromagnetic Model Based on Clinical Magnetic Resonance Images, IEEE, 2010, 4 pages.
J. Clegg et al., A Genetic Algorithm for Optimizing Multi-Pole Debye Models of Tissue Dielectric Properties, Phys. Med. Biol. 57, 2012, pp. 6227-6243.
J.M. Sill et al., Realistic Breast Models for Second Generation Tissue Sensing Adaptive Radar System, The Second European Conference on Antennas and Propagation, 2007, 4 pages.
James et al., Direct Use of CT Scans for Hyperthermia Treatment Planning, IEEE Transactions on Biomedical Engineering, 1992, pp. 845-851, vol. 39, Issue 8.

(56) References Cited

OTHER PUBLICATIONS

Jeremie Bourqui et al., Balanced Antipodal Vivaldi Antenna With Dielectric Director for Near-Field Microwave Imaging, IEEE Transactions on Antennas and Propagation, vol. 58, No. 7, Jul. 2010, pp. 2318-2326.
M. Cavagnaro et al., Water Content Evaluation of a Human Tissue Using Magnetic Resonance Imaging: A Quantitative Benchmarking Approach, 2012 International Symposium on Electromagnetic Compatibility, IEEE, 2012, 6 pages.
M. Mazzurana et al., A Semi-Automatic Method for Developing an Anthropomorphic Numerical Model of Dielectric Anatomy by MRI, Physics in Medicine and Biology 48, 2003, pp. 3157-3170.
M. O'Halloran et at., Rotating Antenna Microwave Imaging System for Breast Cancer Detection, Progress in Electromagnetics Research, vol. 107, 2010, pp. 203-217.
M. R. Sentinella et al., Enhanced Continuous Tabu Search In A Hybrid Evolutionary Algorithm For The Optimization of Interplanetary Trajectories, 21st International Symposium on Space Flight Dynamics, 2009, Toulouse, France, 12 pages.
Manuela Maffongelli et al., Preliminary Test of a Prototype of Microwave Axial Tomograph for Medical Applications, IEEE MeMeA, May 2015. pp. 46-51.
Mariya Lazebnik et al., A Large-Scale Study of the Ultrawideband Microwave Dielectric Properties of Normal Breast Tissue Obtained From Reduction Surgeries, Phys. Med. Biol. 52, 2007, pp. 2637-2656.
Mariya Lazebnik et al., A Large-Scale Study of the Ultrawideband Microwave Dielectric Properties of Normal, Benign and Malignant Breast Tissues Obtained from Cancer Surgeries, 2007, Physics in Medicine and Biology, 52, pp. 6093-6115, IOP Publishing, UK.
Mariya Lazebnik et al., Highly Accurate Debye Models for Normal and Malignant Breast Tissue Dielectric Properties at Microwave Frequencies, IEEE Microwave and Wirless Components Letters, vol. 17, No. 12, Dec. 2007, pp. 822-824.
Mark Converse et al., A Computational Study of Ultra-Wideband Versus Narrowband Microwave Hyperthermia for Breast Cancer Treatment, IEEE Transactions on Microwave Theory and Techniques, vol. 54, No. 5, May 2006, pp. 2169-2180.
Marta Guardiola Garcia, UWB Tomography for Breast Tumor Detection, Master Thesis Dissertation, Universitat Politecnica de Catalunya, Sep. 2009, Barcelona, 64 pages.
Marta Cavagnaro et al., From Magnetic Resonance Imaging To Dielectric Properties of Tissues, Biophysics & Bioeng. Letters, 2011, vol. 4 (2), pp. 1-8.
Meaney et al., Clinical Microwave Tomographic Imaging of the Calcaneus: A First-in-Human Case Study of Two Subjects, IEEE Transaction on Biomedical Engineering, 2012, pp. 3304-3313.
Natalia K. Nikolova, Microwave Imaging for Breast Cancer, IEEE Microwave Magazine, Dec. 2011, pp. 78-94.
P. Fatourous et al., Use of Magnetic Resonance Imaging for in Vivo Measurements of Water Content in Human Brain: Method and Normal Values, J. Neurosurg 90, Jan. 1999, pp. 109-115.
Paolo Farace et al., An Automated Method for Mapping Human Tissue Permittivities by MRI in Hyperthermia Treatment Planning, Phys. Med. Biol. 42, 1997, pp. 2159-2174.
Qing Huo Liu et al., Active Microwave Imaging I—2-D Forward and Inverse Scattering Methods, IEEE Transactions on Microwave Theory and Techniques, Jan. 2002, pp. 123-133, vol. 50, No. 1.
S. Gabriel et al., The Dielectric Properties of Biological Tissues: II., Measurements in the Frequency Range 10 Hz to 20 Ghz, Phys. Med. Biol. 41, 1996, pp. 2251-2269.
S. Gabriel et al., The Dielectric Properties of Biological Tissues: III., Parametric Models for the Dielectric Spectrum of Tissues, Phys. Med. Biol. 41, 1996, pp. 2271-2293.
S. N. Hornsleth et al., A New CT Segmentation Algorithm For Finite Difference Based Treatment Planning Systems, Hyperthermic Oncology, 1996, vol. 2, pp. 521-523.
Susan Rae Smith et al., Dielectric Properties of Low-Water-Content Tissues, Phys. Med. Biol, 1985, vol. 30, No. 9, pp. 965-973.
Thomas Meissner et al., The Complex Dielectric Constant of Pure and Sea Water From Microwave Satellite Observations, IEEE Transactions on Geoscience and Remote Sensing, vol. 42, No. 9, Sep. 2004, pp. 1836-1849.
USPTO Notice of Allowance, U.S. Appl. No. 14/069,661, dated Apr. 14, 2015, 10 pages.
USPTO Office Action, U.S. Appl. No. 14/069,661, dated Feb. 6, 2015, 19 pages.
Uwe Schneider et al., The Calibration of CT Hounsfield Units for Radiotherapy Treatment Planning, Phys. Med. Biol., 41, 1996, pp. 111-124.
W. Shao et al., Multi-Polarized Microwave Power Imaging Algorithm for Early Breast Cancer Detection, Progress in Electromagnetics Research M, vol. 23, 2012, pp. 93-107.
Wenyi Shao et al., Two Antipodal Vivaldi Antennas and an Antenna Array for Microwave Early Breast Cancer Detection, Microwave and Optical Technology Letters, vol. 55, No. 3, Mar. 2013, pp. 670-674.
Wenyi Shao et al., UWB Imaging with Multi-Polarized Signals for Early Breast Cancer Detection, IEEE, 2010, 4 pages.
Wilfried Schneider et al., Correlation Between CT Numbers and Tissue Parameters Needed for Monte Carlo Simulations of Clinical Dose Distributions, Phys. Med. Biol. 45, 2000, pp. 459-478.
Xiaodong Zhuge et al., Circularly Tapered Antipodal Vivaldi Antenna for Array-Based Ultra-Wideband Near-Field Imaging, Proceedings of the 6th European Radar Conference, 2009, pp. 250-253.
Xu Li et al., An Overview of Ultra-Wideband Microwave Imaging via Space-Time Beamforming for Early-Stage Breast-Cancer Detection, IEEE Antennas and Propagation Magazine, Feb. 2005, pp. 19-34, vol. 47, No. 1.
Yao Xie et al., Multistatic Adaptive Microwave Imaging for Early Breast Cancer Detection, IEEE Transactions on Biomedical Engineering, Aug. 2006, pp. 1647-1657, vol. 53, No. 8.
Zastrow et al., Development of Anatomically Realistic Numerical Breast Phantoms With Accurate Dielectric Properties for Modeling Microwave Interactions With the Human Breast, IEEE Transactions on Biomedical Engineering, 2008, pp. 2792-2800, vol. 55, Issue 12.
Zhong Qing Zhang et al., Three-Dimensional Nonlinear Image Reconstruction for Microwave Biomedical Imaging, IEEE Transactions on Biomedical Engineering, Mar. 2004, pp. 544-548, vol. 51, No. 3.

* cited by examiner

MICROWAVE IMAGING DEVICE

BACKGROUND

The inventive concepts disclosed herein relate generally to the field of image processing, and more specifically to a microwave image processing system ideally operating in the frequency range from 300 MHz to 300 GHz.

Microwave imaging is a field of research that attempts to solve the inverse scattering problem. When radio frequency (RF) energy moves through air and impinges on an object, scattering from the object occurs as the RF energy hits the surface and moves through the object. The idea of the inverse scattering problem is to measure this scattering field and, combined with other information about the object, determine an "image" of the object that created the measured scattered field. Microwave imaging has been used for imaging objects such as, for example, the entire, or parts of, the human body.

SUMMARY OF THE INVENTION

According to one embodiment there is provided a microwave (MW) system. The MW system comprises: an object support adapted to support an object; a MW transmitter configured to transmit a MW towards the object; a MW receiver configured to detect a MW scattered field received from the object; an outer rotation unit having a center axis, the outer rotation unit comprises an outer ring, having a ring shape, with an outer ring mount, upon which one of either an antenna of the MW transmitter or an antenna of the MW receiver is mounted; an inner rotation unit, the inner rotation unit comprises an inner ring, having a ring shape, with an inner ring mount, upon which the other of an antenna of the MW transmitter or an antenna of the MW receiver is mounted, the inner ring being concentric to and having a different radius than the outer ring; a controller configured to independently control both the rotation of the inner ring and the outer ring; and a computation processor configured to receive data including MW data representative of the MW scattered field detected by the MW receiver.

According to an aspect, the outer rotation unit further comprises: an outer ring gear fixed to the outer ring; an outer ring pinion gear engaged with the outer ring gear; and a first motor arranged to drive, via a first shaft, the outer ring pinion gear engaged with the outer ring gear such that the outer ring rotates about the center axis.

According to an aspect, the inner rotation unit further comprises: an inner ring gear fixed to the inner ring; an inner ring pinion gear engaged with the inner ring gear; and a second motor arranged to drive, via a second shaft, the inner ring pinion gear engaged with the inner ring gear such that the inner ring rotates about the center axis.

According to an aspect, the system further comprises: a z-axis actuator configured to drive the object support in the vertical direction.

According to an aspect, the system further comprises a first cable arranged to transmit a MW signal from a MW signal generator or vector network analyzer to an antenna of the MW transmitter; and a second cable arranged to transmit a MW signal from an antenna of the MW receiver to a vector network analyzer or oscilloscope.

According to an aspect, the system further comprises a first slip ring supporting the first cable, and arranged to prevent the first cable from wrapping around, and a second slip ring supporting the second cable, and arranged to prevent the second cable from wrapping around.

According to an aspect, the system further comprises a feedback monitor arranged to measure the rotation of at least one of the inner ring or the outer ring and communicate with the controller to adjust the rotation if a mismatch is determined.

According to an aspect, the MW transmitter comprises a plurality of MW transmitter antennas, and the MW receiver comprises a plurality of MW receiver antennas.

According to an aspect, the controller is further configured to control the vertical direction of the object support using the z-axis actuator.

According to an aspect, the computation processor is further configured to reconstruct a dielectric image of the object from the MW data.

According to an aspect, the system further comprises: an object surface position sensor configured to measure the position of a surface of the object over three dimensions to provide object surface position data; a z-axis actuator configured to drive the object support in the vertical direction; wherein the object surface position sensor is mounted to either the outer ring or inner ring; wherein the controller is further configured to control the vertical direction of the object support via the z-axis actuator.

According to an aspect, the computation processor is further configured to receive object surface position data provided by the object surface position sensor and process object surface position data.

According to an aspect, the processed object surface position data comprises smoothed and resampled object surface position data.

According to an aspect, the object surface position sensor comprises: a radiation source; and a photodetector.

According to an aspect, the computation processor is further configured to reconstruct a dielectric image of the object from the MW data and use object surface position data for a seed in the reconstruction.

According to an aspect, the computation processor is remote from at least one of the object surface position sensor, an antenna of the MW transmitter, or an antenna of the MW receiver and comprises at least two centralized processors.

According to an aspect, the computation processor is further configured to reconstruct a dielectric image of the object from the MW data and use at least both of (1) object surface position data and (2) stored data of a prior microwave image reconstruction which closely matches data of the object, to seed the current reconstruction.

According to an aspect, the computation processor is further configured to reconstruct a dielectric image of the object from the MW data and use a seed determined from at least all of (1) comparing scattered fields of current microwave scan to scattered fields of prior microwave scans stored in a database, (2) comparing processed object surface position data of the current microwave scan to prior processed object surface position data stored in a database, and (3) associating scattered fields of prior microwave scans to reconstructed dielectric images of prior microwave scans stored in a database based on said comparisons.

According to an aspect, the computation processor is further configured to convert a reconstructed dielectric image represented in dielectric values to an image represented in Hounsfield units.

According to another embodiment there is provided a method for producing microwave (MW) images. The method comprises: transmitting a MW from a MW transmitter towards an object; detecting, with a MW receiver, a MW scattered field received from the object; controlling a rotation of the MW transmitter and the MW receiver about a center axis; measuring, with an object position sensor, the position of a surface of the object over three dimensions to form object surface position data; controlling a rotation of the object position sensor about a center axis; controlling a vertical direction of the object; determining a seed for reconstruction of an image based in part on the object surface position data, the seed having a surface coinciding with the object surface position data, and based on stored data of a prior microwave image reconstruction which closely matches data of the object. reconstructing an image of the object using the seed and MW data representative of the MW scattered field detected by the MW receiver.

According to an aspect, the method further comprises converting the reconstructed dielectric image represented in dielectric values to an image represented in Hounsfield units.

According to an aspect, the method further comprises processing the object surface position data through the use of smoothing and resampling to provide processed object surface position data.

According to another embodiment there is provided a MW system. The system comprises: an object support adapted to support an object; a MW transmitter configured to transmit a MW towards the object; a MW receiver configured to detect a MW scattered field received from the object; a first antenna mount having both of (1) a lower mount and (2) a radial translation unit having a translation stage upon which one of either an antenna of the MW transmitter or an antenna of the MW receiver is mounted; a second antenna mount having both of (1) a lower mount and (2) a radial translation unit having a translation stage upon which the other of an antenna of the MW transmitter or an antenna of the MW receiver is mounted; a controller configured to control the radial translation stages to translate radially to and from a center axis; and a computation processor configured to receive data including MW data representative of the MW scattered field detected by the MW receiver.

According to an aspect, each of the radial translation units comprise: a gear engaging a respective translation stage; and a motor driving the gear to drive the respective translation stage.

According to another embodiment there is provided a MW system. The MW system comprises: an object support adapted to support an object; a MW transmitter configured to transmit a MW towards the object; a MW receiver configured to detect a MW scattered field received from the object; a controller programmed to include a control module to control the position of an antenna of the MW transmitter, an antenna of the MW receiver, and the object support; a computation processor configured to receive data including MW data representative of the MW scattered field detected by the MW receiver; wherein the control module comprises: providing a user an interface to input conditions for data collection, the conditions including positions of an antenna of the MW transmitter, an antenna of the MW receiver, and of the object support during data collection and names and locations of the to be collected data for storage; and allowing for data including MW data representative of the MW scattered field detected by the MW receiver to be automatically collected and stored based on user input conditions input by the user.

According to an aspect, the control module further comprises: retrieving at least one of (1) previously taken calibration data and (2) instrument parameters, wherein the MW data is automatically collected based in part on the retrieved previously taken calibration data and/or instrument parameters.

According to an aspect, the control module further comprises: allowing for calibration of initial positions of an antenna of the MW transmitter and an antenna of the MW receiver.

DETAILED DESCRIPTION

Modeling of RF scattering problems on the scale of the human body is a very computationally intensive task. Solving the inverse scattering problem requires not only solving the forward scattering problem but then using additional computationally intensive algorithms to complete the solution for solving the inverse problem (i.e., create an image). As a result, the overall solution to MWI (microwave imaging), and reconstructing a microwave image of an object based on microwave data including the MW scattered fields of the object, is a computationally heavy and expensive endeavor. A microwave image is usually an image represented in dielectric values consisting of the permittivity and conductivity.

Techniques for MW reconstruction are provided in, for example, U.S. application Ser. No. 13/798,428, entitled "DISTRIBUTED MICROWAVE IMAGE PROCESSING SYSTEM," filed Mar. 13, 2013, which is incorporated herein by reference in its entirety for devices, methods and techniques related to microwave imaging. Background on microwave imaging is set forth in the following texts: Matteo Pastorino, "Microwave Imaging," WILEY, 2010; Jaleel Akhtar, "Microwave Imaging: Reconstruction of One Dimensional Permittivity Profiles," VDM Verlag, 2008; and Bindu Gopinathan Nair, "Active Microwave Imaging for Mammography: Microwave Medical Imaging," Lap Lambert Academic Publishing, 2012.

Algorithms for reconstructing a microwave image can be iterative or not iterative. In iterative algorithms, the number of iterations may be reduced by providing a good initial estimate, or seed, of the object being imaged. The seed is an initial estimate of the electrical properties of the subject object. For example, if the object being imaged is a human body of a patient, prior MW scan data including a prior microwave image reconstruction of a similar patient may be used as the seed, where the patient and the similar patient are similar in sex, age, weight and/or location of scanned data as described in U.S. application Ser. No. 13/798,428, entitled "DISTRIBUTED MICROWAVE IMAGE PROCESSING SYSTEM," filed Mar. 13, 2013, which is incorporated by reference in its entirety for devices, methods and techniques related to microwave imaging. Even in non-iterative reconstruction algorithms reducing computational demands can be achieved using knowledge of the surface of the object.

The present inventors have realized that the seed may be further enhanced based on the position of the surface of the object being imaged. Thus, the position of the surface of the object may be measured in three dimensions, and that surface position data used to enhance the initial seed.

Microwave Imaging System

Figure 1A:
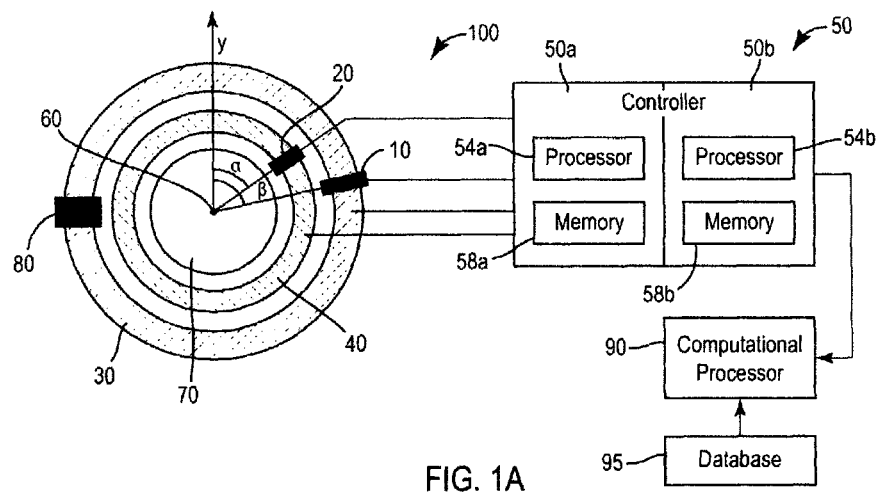
FIG. 1A is a schematic illustrating a microwave imaging system according to an embodiment of the inventive concepts disclosed herein.

FIG. 1A is a schematic of a microwave imaging system 100 according to the inventive concepts disclosed herein. The system 100 includes a MW transmitter antenna 10 configured to emit MW radiation, and a MW receiver 20 antenna configured to detect MW scattered fields from the object. One of the MW transmitter antenna 10 and the MW receiver antenna 20 is mounted on one of an outer rotation unit 30 and an inner rotation unit 40, while the other of the MW transmitter antenna 10 and the MW receiver antenna 20 is mounted on the other of the outer rotation unit 30 and the inner rotation unit 40. Thus, each of the outer rotation unit 30 and the inner rotation unit 40 has one of the MW transmitter antenna 10 and the MW receiver antenna 20 mounted thereon.

The MW transmitter antenna 10 and the MW receiver antenna 20 may be any MW antennas appropriate for microwave imaging. For example, for biomedical imaging, an appropriate antenna to operate over ultra-wideband frequencies is described in U.S. application Ser. No. 14/054,105 entitled "ANITPODAL VIVALDI ANTENNA ARRAY FOR BIOMEDICAL IMAGING," filed Oct. 15, 2013, incorporated herein in its entirety for devices, methods and techniques related to microwave imaging. The MW transmitter antenna 10 and the MW receiver antenna 20 may comprise any antenna including an antipodal Vivaldi antenna. In certain embodiments the antennas used may be patch antennas, multi-band antennas, or monopole antennas. The size of the antennas will vary depending upon the application.

The microwave imaging system 100 may further have a controller 50. The controller 50 is configured to control the outer rotation unit 30 and the inner rotation unit 40 so that the MW transmitter antenna 10 and the MW receiver antenna 20 may be rotated about a center axis 60, which points out of the page in the z-direction in FIG. 1A. Each of the outer rotation unit 30 and the inner rotation unit 40 allows for rotation of a respective of the MW transmitter antenna 10 and the MW receiver antenna 20 from 0° to 360° about the center axis 60. The controller 50 may further be configured to control the MW transmitter antenna 10 to cause the MW transmitter antenna 10 to emit MW radiation, and to control the MW receiver antenna 20 to detect a MW scattered field, and further to collect MW data from the MW receiver antenna 20. In some embodiments, the center axis 60 may be pointed in the x or y directions in FIG. 1A.

The microwave imaging system 100 may have an object mount 70, upon which an object is mounted. The object mount 70 may be moved along the center axis 60 direction, i.e., along the z-axis. In some embodiments, the object may be placed in a tank with an open enclosure filled with a matching medium or liquid. The tank that the object is placed in is then mounted to the object mount 70. In some embodiments the object mount 70 may instead be moved along the x-axis or y-axis.

The controller 50 may include subcontrollers 50a and 50b. The subcontroller 50a may be configured to control the outer rotation unit 30 and the inner rotation unit 40 so that the MW transmitter antenna 10 and the MW receiver antenna 20 may be rotated about the center axis 60. The subcontroller 50b may be configured to control the MW transmitter antenna 10 to cause the MW transmitter antenna 10 to emit MW radiation, and to control the MW receiver antenna 20 to detect MW scattered fields, and further to collect MW data from the MW receiver antenna 20. The controller 50 provides for collection of data by changing the positions of the MW transmitter antenna 10 and the MW receiver antenna 20 by rotation of the outer rotation unit 30 and the inner rotation unit 40, and collecting data at each of the positions. The positions may be changed in stepwise manner, for example, and data collected at each step.

The subcontroller 50a may comprise a processor 54a and memory 58a, so as to allow the subcontroller 50a to perform its control functions. The subcontroller 50a may be hardwired and/or may contain software and programs to allow the subcontroller 50a to perform its control functions. Similarly, the subcontroller 50b may comprise a processor 54b and memory 58b, so as to allow the subcontroller 50b to perform its control functions. The subcontroller 50b may be hardwired and/or may contain software and programs to allow the subcontroller 50b to perform its control functions.

Alternatively, the controller 50 need not include subcontrollers to perform its control functions, or may include more than two subcontrollers. Each of the subcontrollers may control one or more functions of the controller 50. The functions of the subcontrollers may include controlling, in addition to changing the positions of the MW transmitter antenna 10 and the MW receiver antenna 20 by rotating the outer rotation unit 30 and the inner rotation unit 40, changing the positions of the object surface position sensor 80 by rotating the outer rotation unit 30 or the inner rotation unit 40, discussed further below, controlling the object mount 70 to move along the center axis 60 direction, i.e., along the z-axis, and to control radial movement to and from the center axis 60 in some embodiments. In some embodiments, the subcontrollers may include controlling the object mount 70 to move along the x-axis or y-axis.

The outer rotation unit 30 and the inner rotation unit 40 may be independently rotated so that the MW transmitter antenna 10 and the MW receiver antenna 20 are independently rotated about the center axis 60 of the outer rotation unit 30 and the inner rotation unit 40. As seen in FIG. 1A, the MW transmitter antenna 10 is at an angular position about center axis 60 corresponding to an angle $\beta$ with respect to the y-axis, which is vertical in FIG. 1A. Similarly, the MW receiver antenna 20 is at an angular position about center axis 60 corresponding to an angle $\alpha$ with respect to the y-axis. The angles $\alpha$ and $\beta$ may be independently varied based on the rotations of the outer rotation unit 30 and the inner rotation unit 40, respectively. Thus, measurements using the MW transmitter antenna 10 and the MW receiver antenna 20 may be taken for any pair of angles α and β, and for a particular position along the z-axis. Thus, two rotation units are used to provide a full range of pairs of angles, and the object mount 70 provides for movement along the z-axis. The position of the object 5 relative to the MW transmitter antenna 10 and the MW receiver antenna 20 may be described in Cartesian or spherical coordinates.

Figure 1B:
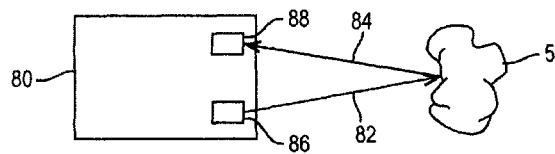
FIG. 1B is a schematic illustrating an object surface position sensor of the microwave imaging system of FIG. 1A.

As illustrated in FIGS. 1A and 1B, the microwave imaging system 100 may have an object surface position sensor 80 configured to measure the surface position of the object 5. The object surface position sensor 80 measures the position of the surface of the object in three dimensional space. The object surface position sensor 80 provides a narrow illumination beam 82 which illuminates the object, and receives a reflection beam 84 back from the object based on the illumination beam 82. Alternatively, the object surface position sensor 80 may receive a reflection beam 84 without providing any illumination beam 82 to illuminate the object. The object surface position sensor 80 can make use of the following equation: $2d = c_0 t$, where d is the distance from object surface position sensor 80 to a point on the object, $c_0$ is the wave speed in air, and t is the time delay. The object surface position sensor 80 measures the distance between the sensor and the object for multiple angular positions to form a contour line. This contour line can be in polar coordinates. A contour line is collected for multiple z-axis positions of the object i.e. the object mount 70 is vertically translated along the center axis 60 direction. In some embodiments, the contour line is collected for multiple x-axis or y-axis positions of the object i.e. the object mount 70 is horizontally translated along the center axis 60 direction.

Figure 1C:
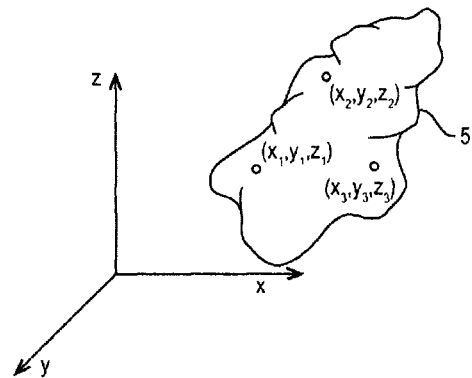
FIG. 1C illustrates a three-dimensional surface of an object.

FIG. 1C illustrates a surface in three dimensions of the object 5, where three points of the object in Cartesian coordinates are shown. While three points of the surface 5 are shown for ease of illustration in FIG. 1C, in practice the object surface position sensor 80 will measure the position of many more points of the surface of the object 5 in a three dimensional space. In an embodiment, once the object surface position in three dimensions is obtained, such as by the object surface position sensor 80, the resulting coordinates obtained are averaged, smoothed, and resampled, or otherwise processed, to form the object surface that is used in practice. Thus, the object surface position data obtained by the sensor 80 may be processed as desired prior to further use.

The object may be moved relative to the sensing beam 82 to provide for a detection of the position of substantially the entire surface of the object. For example, the object may be vertically translated and rotated about the center axis 60 relative to the sensing beam 82. To achieve the relative motion, the object may be vertically translated via the object mount 70, and the surface position sensor 80 may be mounted on the outer rotation unit 30 or the inner rotation unit 40 so as to rotate the surface position sensor 80 about the center axis 60. To collect the full surface of the object the object surface position sensor mounted on one of the rotation units is progressively rotated from 0° to 360° about the center axis 60. As an alternative to achieve relative rotation, the object mount 70 may be rotated about the center axis 60. In one embodiment, the object surface position data is obtained by progressively rotating from 0 to 360° the surface position sensor 80 mounted on one of the rotation units for a series of consecutive object mount 70 positions.

The surface position sensor 80 may comprise an IR sensor which radiates and detects IR radiation from the surface of the object via a photodetector 88. Alternatively, the surface position sensor 80 may include a radiation source 86, such as a laser or light emitting diode, to provide the sensing beam 82, and the photodetector 88 to detect the reflection beam 84. The surface position sensor 80 may comprise a photographic device, such as a camera.

The system 100 may include a computation processor 90 which receives data including MW data representative of the MW scattered field from the controller 50 and which receives the object surface position data from controller 50, and performs MW image reconstruction of the object based on the MW data, object surface position data, and data from database 95. The data in database 95 may be prior collected MW data including MW incident fields, MW scattered fields, object surface position data, and reconstructed dielectric images. The computational processor 90 may comprise one or more subprocessors. The computational processor 90 is not just limited to one processor and may contain at least two processors which employ parallel computing techniques. In addition, the computation processor 90 may comprise both central processing units and graphics processing units. In one embodiment, the two processors are employed in two high performance computers networked together using Infiniband® network cards. Alternatively, the computational processor 90 may transmit and receive data including MW scattered fields and object position data to and from a remote centralized processor and remote database. Remote as used herein can mean in a different room or different building in addition to meaning many miles away. The computation processor 90 may be remote from the object surface position sensor 80, the MW transmitter antenna 10, and the MW receiver antenna 20.

Rotation and Support System

Figure 2:
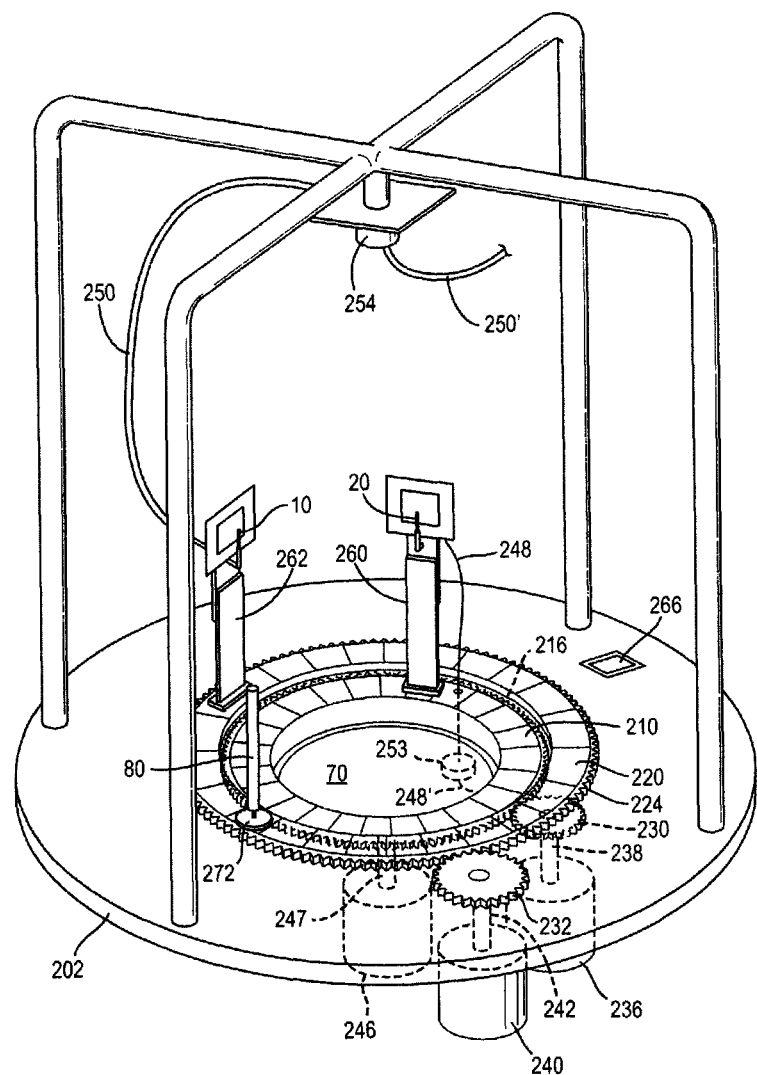
FIG. 2 is a perspective view of a rotation and support system of a microwave imaging system according to an embodiment of the inventive concepts disclosed herein.
Figure 3:
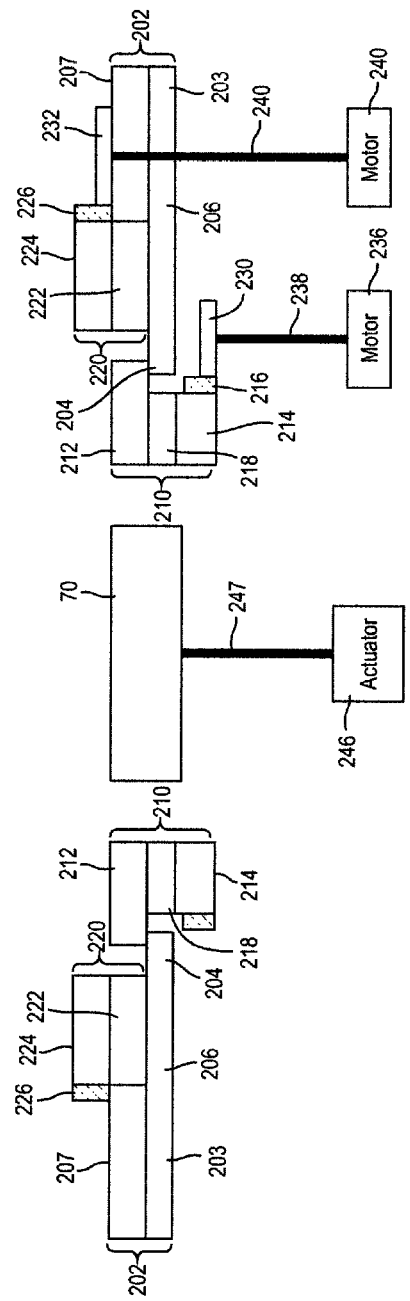
FIG. 3 is a side cross-sectional view of a portion of the rotation and support system of FIG. 2.

FIGS. 2 and 3 illustrate a rotation and support system 200 for the MW transmitter antenna 10 and the MW receiver antenna 20 for the microwave imaging system 100 according to an embodiment of the invention.

The rotation and support system 200 includes a support 202 which includes a support surface mount 207, and a rotation surface mount 203. The rotation surface mount 203 includes an inner ring support region 204 and an outer ring support region 206. The inner ring support region 204 supports an inner ring 210, while the outer ring support region 206 supports an outer ring 220.

The inner ring 210 has an inner ring mount 212, an inner gear ring 214 with inner gear ring teeth 216 and a spacer 218 between the inner ring mount 212 and the inner gear ring 214. A bottom surface of the inner ring mount 212 is supported by a top surface of inner ring support region 204, which may be in the form of a lip, on the inner ring support region 204. The region of contact between the inner ring support region 204 and the inner ring mount 212 may include a friction reducing substance to reduce the friction between the inner ring support region 204 and the inner ring mount 212 when the inner ring 210 is rotating relative to the support 202.

The outer ring 220 has an outer ring mount 222, and an outer gear ring 224 with outer gear ring teeth 226. A bottom surface of the outer ring mount 222 is supported by a top surface of outer ring support region 206. The region of contact between the outer ring mount 222 and the outer ring support region 206 may include a friction reducing substance to reduce the friction between outer ring mount 222 and the outer ring support region 206 when the outer ring 220 is rotating relative to the support 202.

The rotation and support system 200 further includes the object mount 70, upon which an object is placed, and a z-axis actuator 246. The z-axis actuator 246 drives the object mount 70 upward or downward via a drive rod 247 along the axis 60 direction, i.e., along the z-axis. The z-axis actuator 246 may be controlled via the controller 50 (see FIG. 1A).

The rotation and support system 200 includes an inner ring pinion gear 230, inner ring stepper motor 236, which may include an encoder, and inner ring drive shaft 238 arranged to drive the inner ring 210 to be rotated. The inner ring pinion gear 230 may be on a bottom surface of the inner ring support 204. The inner gear ring teeth 216 of the inner gear ring 214 engage with the inner ring pinion gear 230. The inner ring stepper motor 236 rotates the inner ring drive shaft 238, which in turn rotates the inner ring pinion gear 230. The rotating inner ring pinion gear 230, which is engaged with the inner gear ring teeth 216 of the inner gear ring 214, thus drives the inner ring 210 about the axis 60 direction.

The rotation and support system 200 includes an outer ring pinion gear 232, outer ring stepper motor 240, which may include an encoder, and outer ring drive shaft 242 arranged to drive the outer ring 220. The outer ring pinion gear 232 may be on a top surface of the support surface mount 207. The outer gear ring teeth 226 of the outer gear ring 224 engage with the outer ring pinion gear 232. The outer ring stepper motor 240 rotates the outer ring drive shaft 242, which in turn rotates the outer ring pinion gear 232. The rotating outer ring pinion gear 232, which is engaged with the outer gear ring teeth 226 of the outer gear ring 224, thus drives the outer ring 220 to be rotated about the axis 60 direction.

The rotation and support system 200 includes an inner ring antenna mount 260 and an outer ring antenna mount 262, which are mounted on the inner ring mount 212 and the outer ring mount 222, respectively. The inner ring antenna mount 260 and outer ring antenna mount 262 may be removed from the inner ring mount 212 and outer ring mount 222. One of the MW transmitter antenna 10 and the MW receiver antenna 20 is mounted on one of the inner ring antenna mount 260 and the outer ring antenna mount 262, while the other of the MW transmitter antenna 10 and the MW receiver antenna 20 is mounted on the other of the inner ring antenna mount 260 and the outer ring antenna mount 262. Thus, each of the inner ring 210 and the outer ring 220 has one of the MW transmitter antenna 10 and the MW receiver antenna 20 mounted thereon. Different size inner ring antenna mounts 260 and outer ring antenna mounts 262 can be used to allow for different sizes of MW transmitter 10 and MW receiver antenna 20 to be used. This is helpful because antennas designed for different frequency ranges come in different sizes.

The inner ring 210 and the outer ring 220 may be independently rotated via the inner ring stepper motor 236 and the outer ring stepper motor 240 so that the MW transmitter antenna 10 and the MW receiver antenna 20 are independently rotated about the center axis 60. Thus, measurements using the MW transmitter antenna 10 and the MW receiver antenna 20 may be taken for any pair of angles α and β, as discussed with respect to FIG. 1A above.

Further, the MW transmitter antenna 10 and the MW receiver antenna 20 may comprise a single MW receiver antenna, and a single MW transmitter antenna. By using only a single MW receiver antenna, and a single MW transmitter antenna, interference of extra antennas with the radiation from the object being investigated may be reduced. In an embodiment, it is also possible to use multiple MW transmitter antennas 10 and the MW receiver antennas 20 which would necessitate the use of multiple inner ring antenna mounts 260 and outer ring antenna mounts 262.

The MW transmitter antenna 10 and the MW receiver antenna 20 may respectively have cables 248 and 250 to conduct MW radiation to or from the antennas. The cables 248 and 250 may be respectively connected to slip rings 253 and 254. The slip rings 253 and 254 allow that the cables 248 and 250 will not wrap around as the inner ring 210 and the outer ring 220 are rotated about the center axis 60. The cables 248 and 250 may connect to the MW transmitter antenna 10 and the MW receiver antenna 20, respectively, via SMA connectors. Cables 248' and 250' connect to slip rings 253 and 254, respectively, and may further connect to a vector network analyzer, arbitrary waveform generator, and/or oscilloscope (not shown). When using an arbitrary waveform generator and oscilloscope, cable 248' is connected to the oscilloscope, and cable 250' is connected to the arbitrary waveform generator.

The microwave imaging system 100 may further include a feedback monitor 266 that measures the rotation of the rings 210 and 220 so as to allow for a closed loop system, where the rotation of the rings 210 and 220 is not only driven, but is measured to allow for correction based on feedback from the feedback monitor 266. The feedback monitor 266 may count outer gear ring teeth 226 of the outer gear ring 224 and the inner gear ring teeth 216 of the inner gear ring 214 to measure the rotation of the rings 210 and 220. There are situations where it is possible for the sub-controller to change the positions of the MW transmitter antenna 10 and the MW receiver antenna 20 by rotating the rings 210 and 220 but where the rotation thought to occur by the subcontroller is different than that measured by the feedback monitor 266. In this situation the feedback monitor 266 would communicate with the subcontroller to ensure the rotation is correct.

The microwave imaging system 100 may further include the object surface position sensor 80 as discussed above with respect to FIG. 1. The object surface position sensor 80 may be mounted on the support surface 207 of the support 202. In one embodiment, the rotation and support system 200 includes an object position sensor mount 272 which may be mounted on the outer ring mount 222. The object surface position sensor 80 is mounted on the object position sensor mount 272. The object position sensor mount 272 may be removed from outer ring mount 222.

The inner rotation unit 40 of FIG. 1A includes the inner ring 210, inner ring mount 212, inner gear ring 214, spacer 218, inner ring pinion gear 230, inner ring stepper motor 236 and inner ring drive shaft 238. The outer rotation unit 30 of FIG. 1A includes the outer ring 220, outer ring mount 222, outer gear ring 224, outer ring pinion gear 232, outer ring stepper motor 240 and outer ring drive shaft 242.

Figure 6A:
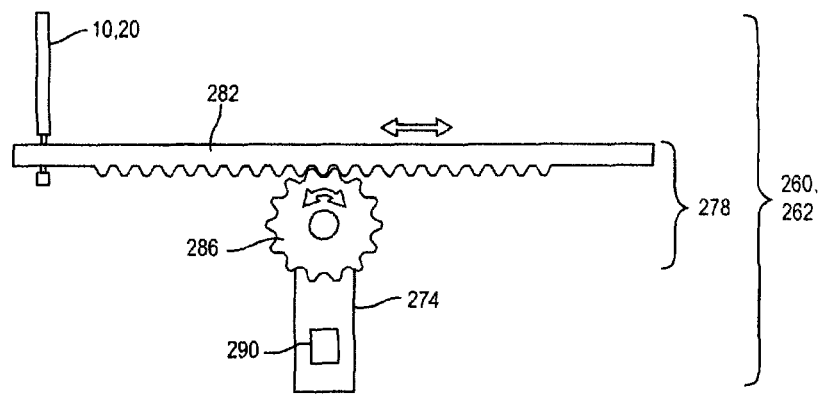
FIG. 6A is a side view of an antenna mount with a radial translation unit according to an embodiment of the inventive concepts disclosed herein.
Figure 6B:
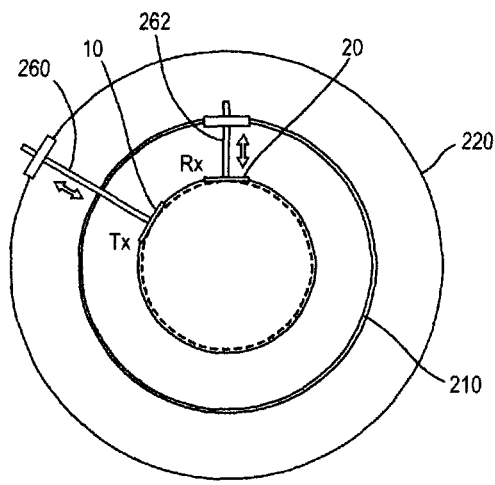
FIG. 6B is a top view of two antenna mounts according to FIG. 6A mounted on the inner and outer rings, respectively.

FIGS. 6A and 6B illustrate an embodiment where the antenna mounts 260 and 262 each include a lower mount and a radial translation unit. Specifically, the antenna mounts 260 and 262 each includes a lower mount 274 and a radial translation unit 278. The radial translation unit 278 includes a translation stage 282, a gear 286 and a motor 290.

In operation, the motor 290 is controlled by the controller 50 so as to rotate the gear 286, which is engaged with teeth of the translation stage 282. Thus, the translation stage 282, which supports one of the MW receiver antenna 20 or the MW transmitter antenna 10, is controlled to translate the antenna along the axial direction to or from the center axis 60.

The radial translation unit 278 allows for more flexibility in positioning the MW receiver antenna 20 or the MW transmitter antenna 10 by including a radial position component. Thus, in this embodiment, the MW receiver antenna 20 and the MW transmitter antenna 10 are not restricted to following a circular path around the center axis. Further, the radial translation unit 278 allows for further flexibility in positioning the MW receiver antenna 20 and the MW transmitter antenna 10 relative to the object 5. The surface position of the object may be measured by the object surface position sensor 80, and then a suitable distance away from the object, such as the closest possible, for the MW receiver antenna 20 and the MW transmitter antenna 10 may be set according to the measured surface position. It has been found that some types of signals like evanescent waves attenuate quickly with the distance away from the surface. Hence, it is possible to detect these types of signals using the radial translation unit 278. In the embodiment shown in FIG. 6B the MW receiver antenna 20 and the MW transmitter antenna 10 are positioned the same distance from the center axis 60. This is not possible without the radial translation unit 278.

The components of the rotation and support system 200 in the vicinity of the object mount 70 and the MW transmitter antenna 10 and MW receiver antenna 20 may be made of a non-metallic material so as to reduce interference with the microwaves emitted and detected, at least in the case where component need not be a metallic material to conduct electricity. The non-metallic material may be plastic, or wood, for example. For example, the support 202, inner ring 210, outer ring 220, pinion gears 230 and 232, and drive shafts may all be made of a non-metallic material.

The size and dimensions of the rotation and support system 200 can be varied to account for different sizes of the object 5. In this way a larger object 5 will necessitate the use of a larger object mount 70. This in turn will necessitate the use of a larger inner ring 210 and outer ring 220. While a smaller object 5 will not require using a smaller object mount 70 and inner and outer rings, the inner ring 210 and outer ring 220 may be made smaller to obtain better image reconstructions. In certain embodiments, the inner ring 210 and the outer ring 220 may be of a size to allow a human body (taken as object 5), or a part of a human body, such as an arm or a leg, to pass within the inner ring 210. Different applications and use cases will require different sized rings.

Reconstruction of Object Image Using Surface Position of Object

Figure 4:
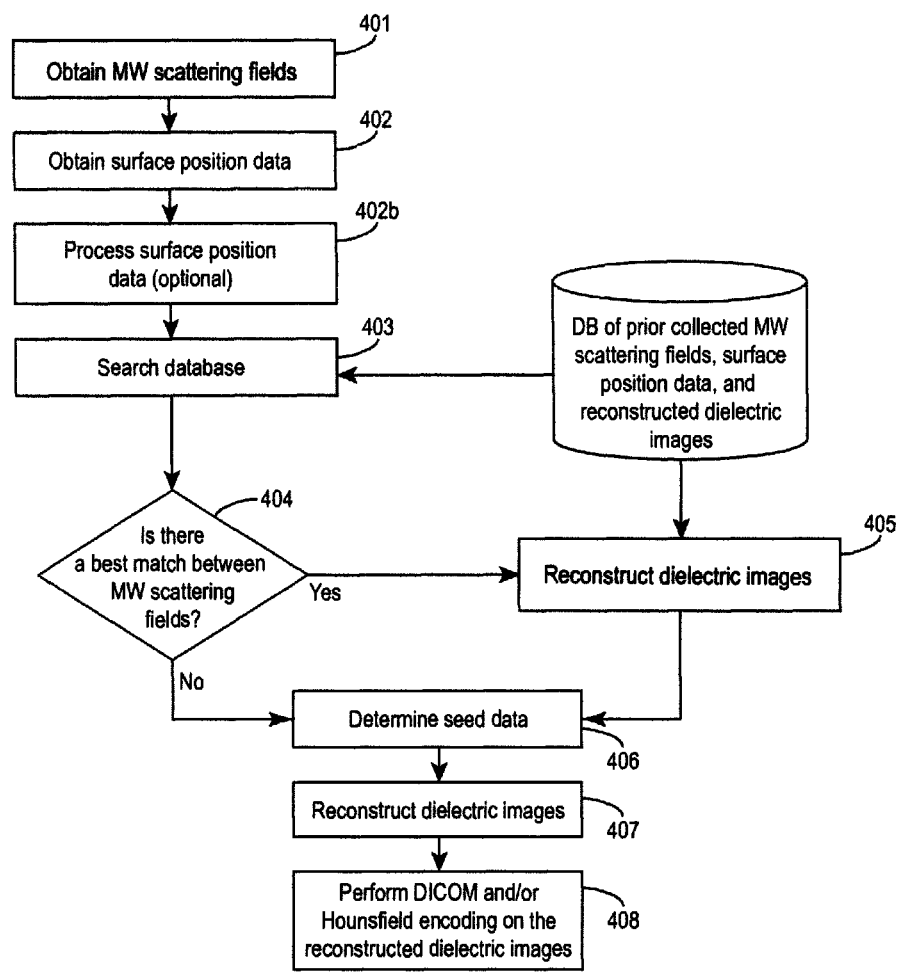
FIG. 4 is a flowchart of exemplary steps used for reconstructing a MW image of an object according to an embodiment of the inventive concepts disclosed herein.

FIG. 4 is a flow chart of exemplary steps used for reconstructing a MW image of an object, such as body of a patient, from data including using measured MW scattered fields and surface position data of the object.

In step 401, MW data including MW scattered fields based on scanning the object is obtained employing measurements using the MW transmitter antenna 10 and the MW receiver antenna 20 which may be angularly rotated and/or z-axis translated relative to the body during a body scan. In an embodiment, the MW transmitter antenna 10 and the MW receiver antenna 20 may be angularly rotated, radially translated, and/or vertically translated relative to the body during a body scan.

Figure 7:
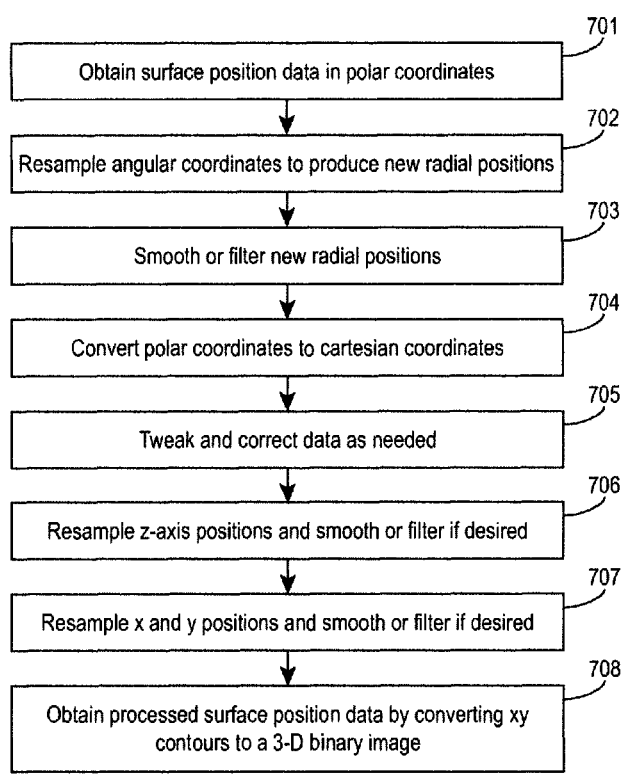
FIG. 7 is a flow chart of steps for processing obtained object surface position data of an object for later use with reconstructing a MW image according to an embodiment of the inventive concepts disclosed herein.

In step 402 surface position data of the surface of the object is obtained. The surface position data may be measured using the object surface position sensor 80. The surface position data may be processed as desired, in step 402b, such as by averaging, applying a smoothing operation, and resampling. FIG. 7 illustrates steps for processing surface position of the step 402b.

FIG. 7 is a flow chart of exemplary steps used in an embodiment for processing obtained object surface position data of an object, such as a body of a patient, for later use with reconstructing a MW image. In step 701, the object surface position sensor 80 collects radial position and records angular position in polar coordinates to obtain object surface position data. Multiple object surface position data for the same angular position and z-axis position can be collected and then the radial position averaged to form the object surface position data. In step 702, for each z-axis position, the angular position collected and radial position is resampled to have angles go from 0 to 360° with a 1° step or some other step. The resampling of the radial position based on the new angles may be done using interpolation. In step 703, smoothing or filtering of the new radial positions, for each z-axis position, is performed. For example, in a filtering step, the Fourier Transform of the new radial positions is taken, the high frequency information is set to zero, and the real component of the Inverse Fourier transform of this result is taken. Alternatively, a moving average of the new radial positions is taken to perform smoothing. In step 704, after the resampling of the new angles and smoothing step occurs, the data is converted from polar coordinates to Cartesian coordinates for each z-axis position. In step 705, additional tweaks and corrections to the obtained resampled and smoothed surface position data in Cartesian coordinates is performed. In some cases, the final contour collected corresponding to the last z-axis position is set to the first contour corresponding to the first z-axis position collected to ensure a full surface position is collected. In some cases, a few contours are ignored such as the top few contours. This is useful such as in some cases there may be errors at the beginning or end of the surface position sensor scan which corresponds to the first few or last few z-axis positions. In step 706, the number of z-axis positions collected is resampled to be different than the actual number of z-axis positions collected. The resampling of the z-axis position is done using interpolation and designed to allow for a finer or coarser resolution in the z-axis. Additional smoothing and filtering operations can be performed if desired after resampling. In step 707, the X and Y coordinates for each contour can be resampled to allow for a finer or coarser resolution. Additional smoothing and filtering operations can be performed if desired after resampling. In step 708, the processed surface position data which can be used for reconstructing a MW image is obtained by converting the xy contours to a binary 3D surface image. Once the contours for each resampled z-axis position is determined they are stacked to form a 3D surface of the object. The 3D surface of the object in X, Y, Z coordinates contains just the contours so only the information corresponding to the surface. To be able to use the 3D surface for use in reconstructing a MW image it is necessary to create a 3D image in pixel values where the pixels on and inside the surface can be distinguished from the pixels outside the surface. The 3D surface of the object X, Y, Z coordinates are converted to pixel values using interpolation or an algorithm to convert each xy contour for each resampled z-axis position into a binary image contained in pixel values where 1 s are inside and include the surface and 0s are outside and exclude the surface or vice versa. A binary 3D image representing the surface of the object is obtained which can be used with reconstructing a MW image.

Referring to FIG. 4, in step 403 a database of prior data is searched. The database includes prior collected MW scattered fields, prior reconstructed dielectric images, and prior surface position data. Associated with the data in the database are other characteristics that were recorded as part of the original scan. These characteristics include the type, frequency, size, and positional information of the MW receiver(s) and transmitter(s), the geometric parameters of the collection device including the size of the inner and outer rings and size of other components as described in FIG. 2 and FIG. 3, calibration data and instrument parameters used during collection, the object classification such as if an animal or human, specific information about the site where the data was collected, demographic information about the patient including sex, age, weight, and height, a reason why the scan was conducted such as any presenting symptoms, and the requested output of the scan including the anatomy and area of interest. The collected MW scattered fields from step 401 and the collected and/or processed surface position data from step 402 along with recorded characteristics such as those described above will get saved into the database along with the later reconstructed dielectric image for use with future MW imaging reconstructions.

This search in step 403 involves looking for prior MW scans that are similar in terms of the MW scattered fields and if available prior surface position data to the current MW scattered field obtained in step 401 and surface position data obtained in step 402. The database is searchable in terms of the MW scattered fields and surface position data and also in other characteristics including patient sex, age, weight, height, and location of the scanned data. In step 404, it is determined if there is a possible best or closest match between the current MW scattered field and prior MW scattered field in the database that can be used. There is a computational component in this block that does further feature extraction and comparisons in order to ensure like data is being compared. The possible match determination involves comparing the obtained MW scattered field in step 401, the obtained surface position data in step 402, and prior data in a database in step 403. In an embodiment, the best match is determined in a series of two consecutive steps. In the first step prior patients similar in MW scattered fields, patient sex, age, weight, height, and location of the scanned data are determined. The minimum sum of the distances taken for all of these characteristics may be used to generate a list of potential prior patients. In the second step the current surface position data from step 402 is compared to the surface position data of the prior patients (from the list of prior patients obtained in the first step). The prior patient that has the surface position data that most closely matches the current surface position data is taken as the best match. In an embodiment, the surface position data of a prior patient may be determined by an edge detection algorithm on the prior reconstructed image obtained in the database. This can be useful when the prior surface position data is missing or absent. In another embodiment, comparison between surface position data of the prior patient to the current patient may be based on minimizing the sum of the distances between the surfaces using imaging processing and optimization techniques.

In step 405, if a best match is found, the prior reconstructed dielectric image of the best match is retrieved from the database of prior data. The database of dielectric images is a database of successfully reconstructed dielectric images. In step 406, if there is a best match in step 404, a seed (initial estimate of the electrical properties of the subject object) is determined based on the prior reconstructed dielectric image retrieved and based on the obtained surface position data from step 402. If there is not a best match in step 404, the seed is determined based on the obtained surface position data, which may be collected surface position data, which has been processed. The seed is then used to reconstruct a dielectric image, described further below.

The seed has a surface coinciding with the obtained object surface position data or very close. That is, the seed is such that the boundary of the object coincides, or is very close, with the object surface position data. For example, if the object, as determined by the surface position sensor, is a sphere with a radius r, the seed may contain an object of a sphere with a radius r. The dielectric values outside the sphere would be assigned values of the medium surrounding the object. The dielectric values inside the sphere would be assigned values based on prior reconstructed dielectric images retrieved if a best match was found or if a best match not found based on prior knowledge or random values using prior knowledge about the range. In the case when a best match is found, there may be slight mismatch between the object as positioned in the prior reconstructed data and the obtained surface position data, but the obtained surface position data may override the prior position data based on the prior reconstructed data retrieved. Alternatively, when a best match is found, the dielectric values of the seed may allow for a slight mismatch between the obtained surface position data and would be based on changing the shape of the prior reconstructed data to closely match the obtained surface position data. In the case when a best match is not found, the dielectric values inside the obtained surface position data is assigned using prior knowledge about the assumed tissues or materials of the object 5. Alternatively, when a best match is not found, the seed is assigned random dielectric values inside the obtained surface position data using prior knowledge about the range of dielectric values for the assumed tissues or materials of the object 5.

As discussed above, this is a substantial feature because iterative reconstruction processing takes substantially less time if a better seed (or starting point) is used. The seed depends not only on the prior reconstructed data from a match, but further depends on the obtained surface position data of the object being investigated. Thus, the system provides for a substantially reduced processing time because voxels outside the object do not have to be reconstructed and the "seed" for the volume outside the object can be assumed to be the medium surrounding the object.

In step 407, the dielectric images are reconstructed using MWI Reconstruction and Learning Algorithms, for example as described in U.S. application Ser. No. 13/798,428, entitled "DISTRIBUTED MICROWAVE IMAGE PROCESSING SYSTEM," filed Mar. 13, 2013, which is incorporated by reference in its entirety. In step 408 (Digital Imaging and Communications in Medicine) DICOM encoding or Hounsfield encoding may be performed on the reconstructed dielectric images, if desired, as described in U.S. application Ser. No. 13/798,428, or U.S. Pat. No. 9,111,334. Step 408 involves converting the raw dielectric image represented in dielectric values to an image represented in Hounsfield units if performing Hounsfield encoding.

Control Module

Figure 5:
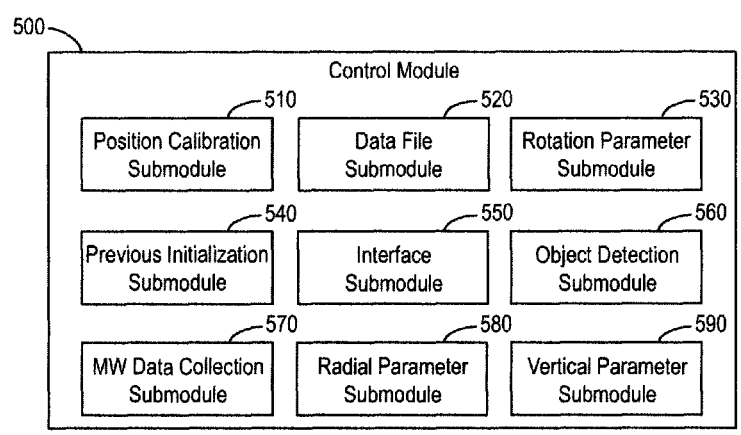
FIG. 5 illustrates a control module, including a plurality of submodules, for automating the data collection according to an embodiment of the inventive concepts disclosed herein.

FIG. 5 illustrates a control module 500 for automating the data collection from the MW transmitter antenna 10 and the MW receiver antenna 20, automating the data collection from the object surface position sensor 80, motor control to control the motors 236, 240, and 290, and actuator control to control the actuator 246. The control module may be implemented on the controller 50 of FIG. 1A as software, firmware or hardware, for example, and may be remote from the site of the MW transmitter antenna 10 and the MW receiver antenna 20.

The control module 500 may include a number of submodules. For example, the control module may include position calibration submodule 510, data file submodule 520, rotation parameter submodule 530, previous initialization submodule 540, interface submodule 550, object detection submodule 560, MW data collection submodule 570, radial parameter submodule 580, and vertical parameter submodule 590.

The position calibration submodule 510 allows for calibration of initial positions of various hardware components. The MW transmitter antenna 10 and the MW receiver antenna 20 initial positions may be calibrated. This is set through the use of the inner ring stepper motor 236 rotating the inner ring 210 and the outer ring stepper motor rotating the outer ring 220. In an embodiment, this is also set through the motor 290 which radially translates the translation stage 282. The feedback monitor 266 may provide feedback on the angular and radial position of the MW transmitter antenna 10 and the MW receiver antenna 20 relative to the object. Further, the initial z-axis position of the object mount 70 may be calibrated through the use of the z-axis actuator 246. In addition, the object surface position sensor 80 may be calibrated through the use of the outer ring stepper motor rotating the outer ring 220. The purpose of using the position calibration submodule 510 is to calibrate the initial positions to known positions so that the parameters of rotations and translations saved are meaningful.

In the data file submodule 520, the folder and storage locations of the data files to be collected and stored are set and if desired an antenna input file is set and the number of data files to collect at the same angular, radial, and vertical position is set. The storage locations may be remote from the site of the MW transmitter antenna 10 and the MW receiver antenna 20. In an embodiment the antenna input file is a signal which is loaded into an arbitrary waveform generator and sent to the MW transmitter antenna 10 via cable 250 which is connected to slip ring 254, and cable 250', which is connected to the arbitrary waveform generator.

In the rotation parameter submodule 530 the minimum and maximum rotation angle and the angular step for the MW transmitter antenna 10 and the MW receiver antenna 20 or object surface position sensor 80 are set. The rotation parameter submodule 530 provides the rotational parameters of the MW transmitter antenna 10 and the MW receiver antenna 20 for a MW data collection scan. The rotation parameter submodule 530 also provides the rotational parameters of the object surface position sensor 80 for an object position sensor data collection scan. This is set through the use of the inner ring stepper motor 236 rotating the inner ring 210 and the outer ring stepper motor rotating the outer ring 220.

In the radial parameter submodule 580 the radial position parameters for the position of the MW transmitter antenna 10 and the MW receiver antenna 20 radially to and from the center axis 60 are set. Thus, the radial parameter submodule 580 provides the radial position parameters of the MW transmitter antenna 10 and the MW receiver antenna 20 for a scan. This is set through the motor 290 which radially translates the translation stage 282.

In the vertical parameter submodule 590 the vertical position parameters for the position of the object mount 70 are set. The vertical position parameters of the z-axis position of the object mount 70 is set through the use of the z-axis actuator 246.

In the previous initialization submodule 540, previously taken calibration data and/or instrument states is retrieved. In an embodiment if using a vector network analyzer, the file containing a prior calibration is loaded. If smoothing of data or averaging of collected data, the desired parameters for this are initialized. The appropriate frequency of the antenna receiver or transmitter being used is selected and a frequency range according to this is set. The number of data points for the measurement is set, as is the RF power level of both ports and the IF bandwidth. In addition, different trigger signal and source parameters are set. Further settings are initialized to allow for the S parameter measurements to be displayed on the vector network analyzer. In a separate embodiment, if using an oscilloscope and arbitrary waveform generator, the waveform to use as a signal for the arbitrary waveform generated is loaded. Various settings on the oscilloscope are initialized for the different channels such as the vertical scale, the horizontal scale, the bandwidth, the trigger level, the sample rate, and the record length. In addition, further settings are initialized to allow for the signal measurements to be displayed on the oscilloscope. Many of the settings from the previous initialization submodule 540 are hardcoded and not selectable or modifiable by the user in interface submodule 550; however, if desired they can be altered and modified.

The interface submodule 550 provides an interface for a user to set up the conditions for the data to be collected and when these conditions are set to collect data. As a first step prior to data collection, it allows a user to set up initial positions via position calibration submodule 510. The MW data and object detection data collections are performed separately and as such have separate conditions set. With the MW data collection, the conditions set up by the user may include, for example, the minimum and maximum rotation angle, the angular step, and the radial positions for both the MW transmitter antenna 10 and the MW receiver antenna 20, the current frequency or frequency range of the MW transmitter antenna 10 and the MW receiver antenna 20, the minimum and maximum vertical position of the object mount 70, the vertical step, if any, the data file names and locations for storing the data files, if desired the number of times data at the same angular, radial, and vertical positions should be collected, and a signal loaded into an instrument. With the object surface position collection, the conditions set up by the user may include the minimum and maximum rotation angle and the angular step for the object surface position sensor 80, the minimum and maximum position of the object mount 70, the vertical step, the data file names and locations for storing the data files, and if desired the number of times data at the same angular, radial, and vertical positions should be collected. The interface submodule sets the conditions for the data to be collected by communicating with data file submodule 520, rotation parameter submodule 530, radial parameter submodule 580, and vertical parameter submodule 590. The interface submodule can call the previous initialization submodule 540 so that previously taken calibration data and/or instrument states is retrieved. The previously taking calibration data and/or instrument state that is retrieved is determined based upon conditions set up by the user in interface submodule 550. The interface submodule further includes safeguards to ensure that the software is successfully communicating with necessary hardware and instruments. If a safeguard fails, the user will be prompted with an error message and given suggestions as to what caused the prompt. Once all the user conditions, initialization, and safeguards are passed the interface allows for an automatic way to collect either MW data via submodule 570 or object detection data via submodule 560. In this sense the interface submodule 550 allows a user to perform all the necessary steps of the other submodules in the control module. In an embodiment, the interface submodule 550 communicates with necessary hardware and instruments (such as a vector network analyzer, oscilloscope and arbitrary waveform generator) using VISA (Virtual Instrument Software Architecture).

The object detection submodule 560 allows for the object surface position to be automatically collected once the conditions for collection are set in the interface submodule 550. The collected data includes the distance from the object surface position sensor 80 to the object as a function of the angular position of object surface position sensor 80, the z axis position of the object mount 70, and if desired, a number to indicate how many times the data at the same angular and z-axis positions was collected.

The MW data collection submodule 570 allows for the MW data to be automatically collected once the conditions for collection are set in the interface submodule 550. The collected data includes MW data representative of the MW scattered field as a function of the MW transmitter antenna 10 and the MW receiver antenna 20 angular and radial positions, the z-axis position of the object mount 70, and if desired, a number to indicate how many times the data at the same angular and z-axis positions was collected.

The embodiments of the inventive concepts disclosed herein have been described in detail with particular reference to preferred embodiments thereof, but it will be understood by those skilled in the art that variations and modifications can be effected within the spirit and scope of the inventive concepts.

REFERENCE NUMERALS

10 MW transmitter antenna
20 MW receiver antenna
30 outer rotation unit
40 inner rotation unit
50 controller
50a subcontroller
50b subcontroller
60 center axis
70 object mount
80 object surface position sensor
82 sensing beam
84 reflection beam
86 radiation source
88 photodetector
90 computation processor
95 database
100 microwave imaging system
202 support
203 rotation surface mount
206 outer ring support region
204 inner ring support region
207 support surface mount
210 inner ring
212 inner ring mount
214 inner gear ring
216 inner gear ring teeth
218 spacer
220 outer ring
222 outer ring mount
224 outer gear ring
226 outer gear ring teeth
230 pinion gear (inner ring)
232 pinion gear (outer ring)
236 stepper motor (inner ring)
240 stepper motor (outer ring)
238 drive shaft (inner ring)
242 drive shaft (outer ring)
246 z-axis actuator
247 drive rod
248, 250 cables
252, 254 slip rings
260, 262 antenna mounts
266 feedback monitor
270 object position sensor mount
274 lower mount
278 radial translation unit
282 translation stage
286 gear
290 motor

What is claimed is:

1. A microwave (MW) system, comprising:
an object support adapted to support an object;
a MW transmitter configured to transmit a MW towards the object;
a MW receiver configured to detect a MW scattered field received from the object;
an outer rotation unit having a center axis, the outer rotation unit comprises an outer ring, having a ring shape, with an outer ring mount, upon which one of either an antenna of the MW transmitter or an antenna of the MW receiver is mounted;
an inner rotation unit, the inner rotation unit comprises an inner ring, having a ring shape, with an inner ring mount, upon which the other of an antenna of the MW transmitter or an antenna of the MW receiver is mounted, the inner ring being concentric to and having a different radius than the outer ring;
a controller configured to independently control both the rotation of the inner ring and the outer ring; and
a computation processor configured to receive data including MW data representative of the MW scattered field detected by the MW receiver.

2. The system of claim 1, wherein the outer rotation unit further comprises:
an outer ring gear fixed to the outer ring;
an outer ring pinion gear engaged with the outer ring gear; and
a first motor arranged to drive, via a first shaft, the outer ring pinion gear engaged with the outer ring gear such that the outer ring rotates about the center axis.

3. The system of claim 1, wherein the inner rotation unit further comprises:
an inner ring gear fixed to the inner ring;
an inner ring pinion gear engaged with the inner ring gear; and
a second motor arranged to drive, via a second shaft, the inner ring pinion gear engaged with the inner ring gear such that the inner ring rotates about the center axis.

4. The system of claim 1, further comprising:
a z-axis actuator configured to drive the object support in the vertical direction.

5. The system of claim 1, further comprising:
a first cable arranged to transmit a MW signal from a MW signal generator or vector network analyzer to an antenna of the MW transmitter; and
a second cable arranged to transmit a MW signal from an antenna of the MW receiver to a vector network analyzer or oscilloscope.

6. The system of claim 5, further comprising:
a first slip ring supporting the first cable, and arranged to prevent the first cable from wrapping around, and
a second slip ring supporting the second cable, and arranged to prevent the second cable from wrapping around.

7. The system of claim 1, further comprising:
a feedback monitor arranged to measure the rotation of at least one of the inner ring or the outer ring and communicate with the controller to adjust the rotation if a mismatch is determined.

8. The system of claim 1, wherein the MW transmitter comprises a plurality of MW transmitter antennas, and the MW receiver comprises a plurality of MW receiver antennas.

9. The system of claim 4, wherein the controller is further configured to control the vertical direction of the object support using the z-axis actuator.

10. The system of claim 1, wherein the computation processor is further configured to reconstruct a dielectric image of the object from the MW data.

11. The system of claim 1, further comprising:
an object surface position sensor configured to measure the position of a surface of the object over three dimensions to provide object surface position data;
a z-axis actuator configured to drive the object support in the vertical direction;
wherein the object surface position sensor is mounted to either the outer ring or inner ring;
wherein the controller is further configured to control the vertical direction of the object support via the z-axis actuator.

12. The system of claim 11, wherein the computation processor is further configured to receive object surface position data provided by the object surface position sensor and process object surface position data.

13. The system of claim 12, wherein the processed object surface position data comprises smoothed and resampled object surface position data.

14. The system of claim 11, wherein the object surface position sensor comprises:
a radiation source; and
a photodetector.

15. The system of claim 11, wherein the computation processor is further configured to reconstruct a dielectric image of the object from the MW data and use object surface position data for a seed in the reconstruction.

16. The system of claim 15, wherein the computation processor is remote from at least one of the object surface position sensor, an antenna of the MW transmitter, or an antenna of the MW receiver and comprises at least two centralized processors.

17. The system of claim 11, wherein the computation processor is further configured to reconstruct a dielectric image of the object from the MW data and use at least both of (1) object surface position data and (2) stored data of a prior microwave image reconstruction which closely matches data of the object, to seed the current reconstruction.

18. The system of claim 11, wherein the computation processor is further configured to reconstruct a dielectric image of the object from the MW data and use a seed determined from at least all of (1) comparing scattered fields of a current microwave scan to scattered fields of prior microwave scans stored in a database, (2) comparing processed object surface position data of the current microwave scan to prior processed object surface position data stored in a database, and (3) associating scattered fields of prior microwave scans to reconstructed dielectric images of prior microwave scans stored in a database based on said comparisons.

19. The system of claim 14, wherein the computation processor is further configured to convert a reconstructed dielectric image represented in dielectric values to an image represented in Hounsfield units.

20. A method for producing microwave (MW) images, comprising:
transmitting a MW from a MW transmitter towards an object;
detecting, with a MW receiver, a MW scattered field received from the object;
controlling a rotation of the MW transmitter and the MW receiver about a center axis;
measuring, with an object position sensor, the position of a surface of the object over three dimensions to form object surface position data;
controlling a rotation of the object position sensor about a center axis;
controlling a vertical direction of the object;
determining a seed for reconstruction of an image based in part on the object surface position data, the seed having a surface coinciding with the object surface position data, and based on stored data of a prior microwave image reconstruction which closely matches data of the object; and
reconstructing an image of the object using the seed and MW data representative of the MW scattered field detected by the MW receiver.

21. The method of claim 20, further comprising converting the reconstructed dielectric image represented in dielectric values to an image represented in Hounsfield units.

22. The method of claim 20, further comprising processing the object surface position data through the use of smoothing and resampling to provide processed object surface position data.

23. A microwave (MW) system, comprising:
an object support adapted to support an object;
a MW transmitter configured to transmit a MW towards the object;
a MW receiver configured to detect a MW scattered field received from the object;
a first antenna mount having both of (1) a lower mount and (2) a radial translation unit having a translation stage upon which one of either an antenna of the MW transmitter or an antenna of the MW receiver is mounted;
a second antenna mount having both of (1) a lower mount and (2) a radial translation unit having a translation stage upon which the other of an antenna of the MW transmitter or an antenna of the MW receiver is mounted;
a controller configured to control the radial translation stages to translate radially to and from a center axis; and
a computation processor configured to receive data including MW data representative of the MW scattered field detected by the MW receiver.

24. The MW system of claim 23, wherein each of the radial translation units comprise:
a gear engaging a respective translation stage; and
a motor driving the gear to drive the respective translation stage.

25. A microwave (MW) system, comprising:
an object support adapted to support an object;
a MW transmitter configured to transmit a MW towards the object;
a MW receiver configured to detect a MW scattered field received from the object;

a controller programmed to include a control module to control the position of an antenna of the MW transmitter, an antenna of the MW receiver, and the object support;

a computation processor configured to receive data including MW data representative of the MW scattered field detected by the MW receiver;

wherein the control module comprises:

providing a user an interface to input conditions for data collection, the conditions including positions of an antenna of the MW transmitter, an antenna of the MW receiver, and of the object support during data collection and names and locations of the to be collected data for storage; and allowing for data including MW data representative of the MW scattered field detected by the MW receiver to be automatically collected and stored based on user input conditions input by the user.

26. The system of claim 25, wherein the control module further comprises:

retrieving at least one of (1) previously taken calibration data and (2) instrument parameters, wherein the MW data is automatically collected based in part on the retrieved previously taken calibration data and/or instrument parameters.

27. The system of claim 25, wherein the control module further comprises:

allowing for calibration of initial positions of an antenna of the MW transmitter and an antenna of the MW receiver.

* * * * *